United States Patent [19]
Colosi

[11] Patent Number: 5,945,335
[45] Date of Patent: Aug. 31, 1999

[54] ADENOVIRUS HELPER-FREE SYSTEM FOR PRODUCING RECOMBINANT AAV VIRIONS LACKING ONCOGENIC SEQUENCES

[75] Inventor: Peter Colosi, Alameda, Calif.

[73] Assignee: Avigen, Inc., Alameda, Calif.

[21] Appl. No.: 09/116,780

[22] Filed: Jul. 16, 1998

Related U.S. Application Data

[63] Continuation-in-part of application No. 08/745,957, Nov. 7, 1996

[60] Provisional application No. 60/006,402, Nov. 9, 1995.

[51] Int. Cl.$^6$ ...................................................... C12N 5/08
[52] U.S. Cl. ..................... 435/369; 435/320.1; 536/23.1; 536/23.72; 536/24.1
[58] Field of Search ................................ 435/320.1, 369; 536/23.1, 23.72, 24.1

[56] References Cited

PUBLICATIONS

"Production of High–Titer Recombinant Adeno–Associated Virus Vectors in the Absence of Helper Adenovirus", Xiao et al., *Journal of Virology*, vol. 72, No. 3, Mar. 1998, pp. 2224–2232.

"Human Adenovirus Early Region 4 Open Reading Frame 1 Genes Encode Growth–Transforming Proteins That May Be Distantly Related to dUTP Pyrophosphatase Enzymes", Weiss et al., *Journal of Virology*, vol. 71, No. 3, Mar. 1997, pp. 1857–1870.

"Oncogenic Potential of the Adenovirus E4orf6 Protein", Moore et al., *Proc. Natl. Acad. Sci.*, vol. 93, Oct. 1996, pp. 11295–11301.

"Adenovirus Type 9 E4 Open Reading Frame 1 Encodes a Transforming Protein Required for the Production of Mammary Tumors in Rats", Javier, *Journal of Virology*, vol. 68, No. 6, Jun. 1994, pp. 3917–3924.

"Locations of Adenovirus Genes Required for the Replication of Adenovirus–Associated Virus", Janik et al., *Proc. Natl. Acad. Sci.*, vol. 78, No. 3, Mar. 1981, pp. 1925–1929.

*Primary Examiner*—James Ketter
*Assistant Examiner*—Irem Yucel
*Attorney, Agent, or Firm*—Madson & Metcalf; Kenneth G. Chahine

[57] ABSTRACT

Composition and methods are provided for producing recombinant AAV ("rAAV") in the absence of helper virus, such as adenovirus. The compositions provide the accessory functions necessary for supporting rAAV virion production in host cells. In certain embodiments, the accessory functions are provided by vectors comprising nucleotide sequences from an adenoviral E4 region which lack the putatively oncogenic E4 ORF 6 coding region. The present invention also includes host cells transfected by the claimed accessory function vectors, methods of using such vectors, and rAAV virions produced by such methods.

21 Claims, No Drawings

ADENOVIRUS HELPER-FREE SYSTEM FOR PRODUCING RECOMBINANT AAV VIRIONS LACKING ONCOGENIC SEQUENCES

1. RELATED APPLICATIONS

This application is a continuation-in-part of copending U.S. patent application Ser. No. 08/745,957 of Peter C. Colosi filed Nov. 7, 1996 and entitled "Accessory Functions for Use in Recombinant AAV Virion Production," which Patent Application is incorporated herein by reference. U.S. patent application Ser. No. 08/745,957 is related to and claims priority under 35 U.S.C. § 119(e)(1) from Provisional Application 60/006,402, filed Nov. 9, 1995. Provisional application 60/006,402 is incorporated herein by reference.

2. FIELD OF THE INVENTION

The present invention relates to adenovirus helper virus regions (E1, VA, E2A and E4) that provide the necessary accessory functions required to rescue and efficiently produce recombinant AAV (rAAV) virions. More specifically, the present invention relates to an adenovirus helper virus E4 region that is free from oncogenic sequences. The putative oncogenic sequences coded by open reading frames ("ORFs") one (1) and six (6) of the adenovirus E4 region have been removed without compromising rAAV virion production efficiency.

3. TECHNICAL BACKGROUND

Gene Therapy

Scientists are continually discovering genes that are associated with human diseases such as diabetes, hemophilia and cancer. Research efforts have also uncovered genes, such as erythropoietin (which increases red blood cell production), that are not associated with genetic disorders but code for proteins that can be used to treat numerous diseases. However, despite significant progress in the effort to identify and isolate genes, a major obstacle facing the biopharmaceutical industry is how to safely and persistently deliver effective quantities of these genes' products to patients.

Currently, the protein products of these genes are synthesized in cultured bacterial, yeast, insect, mammalian, or other cells and delivered to patients by intravenous injection. While intravenous injection of recombinant proteins has been successful, it suffers from several drawbacks. First, patients frequently require multiple injections in a single day in order to maintain the necessary levels of the protein in the blood stream. Even then, the concentration of protein is not maintained at physiological levels—the level of the protein is usually abnormally high immediately following injection and far below optimal levels prior to injection. Second, intravenous delivery often cannot deliver the protein to the target cells, tissues or organs in the body. And, if the protein reaches its target, it is often diluted to non-therapeutic levels. Third, the method is inconvenient and severely restricts the patient's lifestyle. The adverse impact on lifestyle is especially significant when the patient is a child.

These shortcomings have led to the development of gene therapy methods for delivering sustained levels of specific proteins into patients. These methods allow clinicians to introduce DNA coding for a gene of interest directly into a patient (in vivo gene therapy) or into cells isolated from a patient or a donor (ex vivo gene therapy). The introduced DNA then directs the patient's own cells or grafted cells to produce the desired protein product. Gene delivery, therefore, obviates the need for daily injections. Gene therapy will also allow clinicians to select specific organs or cellular targets (e.g., muscle, blood cells, brain cells, etc.) for therapy.

DNA may be introduced into a patient's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery methods include retrovirus, adenovirus, herpes virus, pox virus, and adeno-associated virus (AAV) vectors. Of the more than 100 gene therapy trials conducted, more than 95% used viral-mediated gene delivery. C. P. Hodgson, Bio/Technology 13, 222–225 (1995).

Adeno-Associated Virus-Mediated Gene Therapy

One viral system that has been used for gene delivery is adeno-associated virus (AAV). AAV is a parvovirus which belongs to the genus Dependovirus. AAV has several attractive features not found in other viruses. First, AAV can infect a wide range of host cells, including non-dividing cells. Second, AAV can infect cells from different species. Third, AAV has not been associated with any human or animal disease and does not appear to alter the biological properties of the host cell upon integration. Indeed, it is estimated that 80–85% of the human population has been exposed to the virus. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs). The ITRs are approximately 145 base pairs (bp) in length. The ITRs have multiple functions, including as origins of DNA replication, and as packaging signals for the viral genome.

The internal non-repeated portion of the genome includes two large open reading frames, known as the AAV replication (rep) and capsid (cap) genes. The rep and cap genes code for viral proteins that allow the virus to replicate and package the viral genome into a virion. In particular, a family of at least four viral proteins are expressed from the AAV rep region, Rep 78, Rep 68, Rep 52, and Rep 40, named according to their apparent molecular wight. The AAV cap region encodes at least three proteins, VP1, VP2, and VP3.

AAV is a helper-dependent virus; that is, it requires co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

AAV has been engineered to deliver genes of interest by deleting the internal non-repeating portion of the AAV genome and inserting a heterologous gene between the ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

To produce infectious rAAV containing the heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus, such as adenovirus.

Once these factors come together, the heterologous gene is replicated and packaged as though it were a wild-type AAV genome. When a patient's cells are infected with the resulting rAAV virions, the heterologous gene enters and is expressed in the patient's cells. Because the patient's cells lack the rep and cap genes and the adenovirus helper genes, the rAAV cannot further replicate and package. Similarly, wild-type AAV cannot be formed.

The use of helper virus, however, presents a number of problems. First, the use of adenovirus in a rAAV production system causes the host cells to produce both rAAV and infectious adenovirus. The contaminating infectious adenovirus can be inactivated by heat treatment (56° C. for 1 hour). Heat treatment, however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus require the use and manipulation of large amounts of high titer infectious helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

These problems have led researchers to determine the gene or genes in adenovirus that provide the accessory functions necessary to produce rAAV virions. Despite a substantial amount of research, a complete set of adenovirus helper genes has not been unambiguously defined, nor has it been demonstrated that the combination of the E1A, E1B, VA RNA, E2A, and E4 genes are alone capable of providing helper functions sufficient to produce levels of rAAV that are comparable to those produced by methods using adenovirus (or other helper virus) infection.

The Adenovirus E4 Region

One of the adenoviral regions required for AAV rescue is the E4 region. E4 is known to contain seven different open reading frames (ORFs): ORF 1, ORF 2, ORF 3, ORF 3/4, ORF 4, ORF 6, and ORF 6/7. Javier, R. T., *J. Virology* 68, 3917–3924 (1994); Cutt, J. R. et al.,*J. Virology* 61, 543–552 (1987). The gene products of four of these ORFs (ORF 3, ORF 4, ORF 6, and ORF 6/7) have been detected in cells.

While using the entire E4 region yields efficient rAAV virion production, there are concerns about using all of the E4 ORFs. For example, Moore and coworkers have demonstrated that the E4 ORF 6 protein is oncogenic. Moore, M. et al.,*Proc. Natl. Acad. Sci. USA* 93, 11,295–11,301 (1996); see also Nevels, M. et al., *Proc. Natl. Acad. Sci. USA* 94, 1206–1211 (1997); Dobner, T. et al., *Science* 272, 1470–1473 (1996). Thus, AAV vectors expressing oncogenic genes may be generated as side products during vector production by recombination of the replicating AAV vectors with oncogenic genes in accessory function plasmids carrying E4 ORF 6. Low levels of non-homologous recombination is known to occur between plasmids carrying rep/cap sequences and the replicating AAV vectors such that the rep/cap sequences are inserted between the AAV ITRs to form a pseudo-wildtype virus. If similar non-homologous recombination would occur, a potentially more dangerous contaminant could be generated and transmitted to the patient.

Several groups have also reported that E4 ORF 1 of type 9 adenovirus elicits estrogen-dependent mammary tumors in rats. Javier, R. et al.,*Science* 257, 1267–1271 (1992); Javier, R., *J. Virology* 68, 3917–3924 (1994); Weiss, R. et al., *J. Virology* 71, 4385–4394 (1997); Lee, S. et al., *Proc. Natl. Acad Sci. USA* 94, 6670–6675 (1997); Weiss, R. et al., *J. Virology* 71, 1857–1870 (1997). Javier (1994), supra, described adenovirus type 9 as being uniquely capable of this transformation, but later reports (see, e.g., Weiss, R. et al., *J. Virology* 71, 1857–1870 (1997)) claimed the conserved ORF 1 sequences of all adenoviruses were capable of cellular transformation if expressed at higher levels. As discussed above for ORF 6, recombination events could place the E4 ORF 1 gene of an accessory function vector behind the heterologous promoter of the rAAV vector.

Removal of these ORFs from the E4 region, has not been thought to be a viable method of generating rAAV. Several groups report that these ORFs—particularly ORF 6—are critical to AAV production. For example, Samulski, R. J. and Shenk, T., *J. Virology* 62, 206–210 (1988), examined a single E4 mutant, dl355, that contains a 14 base pair deletion in the ORF 6-specific sequence. In wild-type AAV production assays, the ORF 6 mutant produced significantly lower titers of AAV virus. The ORF 6 mutant yielded 2% and 40% of the AAV titers produced by adenovirus helper virus infection at 40 and 80 hours, respectively. AAV production using adenovirus helper virus infection reaches maximal levels at 40 hours.

In another example, Huang and Hearing constructed an extensive set of E4 ORF mutants and tested the corresponding mutant adenovirus strains for the ability to mediate AAV genome replication. Huang, M. M. and Hearing, P., *J. Virology* 63, 2605–2615 (1989). The AAV sequences were provided to the producer cell line by transfection of the pSM620 provirus (to examine the effect on excision) and by infection with AAV (to examine the effect on replication in the absence of excision). The only endpoint tested was AAV genome replication at 40 hours, and no attempt was made to quantify the production of functional virus. The authors concluded that only E4 ORF 6 mediates AAV genome accumulation at 40 hours. These studies strongly suggest that the E4 ORF 6 gene product is an important, if not essential, component in AAV production.

From the foregoing, it will be appreciated that it would be a significant advancement in the art to provide accessory functions for rAAV production without using infectious helper virus. It would be a further advancement in the art to provide such functions without the risk of transmitting oncogenic nucleotide sequences to a patient's cells.

Such accessory functions and methods of their use are disclosed herein.

4. BRIEF SUMMARY OF THE INVENTION

The present invention relates to E1A, E1B, VA, E2A and E4 regions in the adenovirus genome, and host cells containing these adenovirus regions, that provide the necessary accessory functions for producing rAAV virion production in the absence of infectious helper virus. In certain embodiments, these accessory function regions comprise nucleotide sequences from an adenoviral E4 region that lacks an intact E4 ORF 6 gene. Surprisingly, deletion of the ORF 6 gene does not affect rAAV virion production efficiency. In certain preferred embodiments, the accessory function regions also lack an intact E4 ORF 1 coding region. Like the ORF 6 deletion, the E4 region lacking the ORF 1 and 6 genes is able to provide accessory function necessary for efficient rAAV virion production.

In another embodiment, the present invention is an accessory system for rAAV production. This accessory system includes at least three accessory function vectors. The first vector provides adenoviral VA RNA sequences. The second vector provides sequences from an adenoviral E4 region lacking an intact E4 ORF 6. The third vector provides sequences that code for an adenoviral E2A and the E2A 72 kD product.

Further embodiments of the present invention include methods of using accessory function vectors and rAAV virions produced by such methods. The rAAV virions produced using the present invention may be used to introduce genetic material into animals, including humans, or isolated animal cells for a variety of research and therapeutic uses. For example, rAAV virions produced during the method of the present invention may be used to express a protein in animals to gather preclinical trial data or to screen for potential drug candidates. Alternatively, the rAAV virions may be used to transfer genetic material into humans to cure a genetic defect or to effect a desired treatment.

These and other objects and advantages of the present invention will become apparent upon reading the following detailed description and appended claims.

5. DETAILED DESCRIPTION OF THE INVENTION

The present invention is directed to novel accessory function vectors for producing rAAV for introducing genetic material into animals or animal cells for a variety of research and therapeutic uses. A physician or researcher may wish to introduce DNA into an organism (or cells isolated from an organism) for any of several reasons. First, DNA may be introduced to correct a defective gene. Second, DNA may be introduced to specifically delete or mutate a given gene by, for example, homologous recombination. Third, DNA may be introduced to express a protein. Such a protein may be expressed to achieve a therapeutic benefit within the organism treated with rAAV. Alternatively, a protein may be expressed in an organism or in cells isolated from an organism with the goal of isolating and purifying the protein product. Unlike previously described methods for producing rAAV, however, the accessory function vectors of the present invention eliminate the need for infectious helper virus and avoid the risks of transmitting oncogenic sequences.

All publications, patents, and patent applications cited herein are hereby incorporated by reference.

DEFINITIONS

In describing the present invention, the following terms will be employed, and are intended to be defined as indicated below.

"Gene transfer" or "gene delivery" refers to methods or systems for reliably inserting foreign DNA into host cells. Gene transfer can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5, 793–801; Bems, K. I. "Parvoviridae and their Replication" in *Fundamental Virology*, 2d ed., (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are required to replicate the viral genome and to insert the viral genome into a host genome during latent infection. The term also includes functional homologues thereof such as the human herpesvirus 6 (HHV-6) rep gene which is also known to mediate AAV-2 DNA replication (Thomson et al. (1994) *Virology* 204, 304–311). For a further description of the AAV rep coding region, see, e.g., Muzyczka, N. (1992) *Current Topics in Microbiol. and Immunol.* 158, 97–129; Kotin, R. M. (1994) *Human Gene Therapy* 5, 793–801. The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

By "AAV cap coding region" is meant the art-recognized region of the AAV genome which encodes the coat proteins of the virus which are required for packaging the viral genome. For a further description of the cap coding region, see, e.g., Muzyczka, N. (1992) *Current Topics in Microbiol. and Immunol.* 158, 97–129; Kotin, R. M. (1994) *Human Gene Therapy* 5, 793–801. The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences that can be expressed to provide AAV gene products that, in turn, function in trans for productive AAV replication. Thus, AAV helper functions include the rep and cap regions. The rep expression products have been shown to possess many functions, including, among others: recognition, binding and nicking of the AAV origin of DNA replication; DNA helicase activity; and modulation of transcription from AAV (or other heterologous) promoters. The cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virology* 63, 3822–3828; McCarty et al. (1991) *J. Virology* 65, 2936–2945. A number of other vectors have been described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures DNAs, RNAs and protein that are required for AAV replication, including those moieties involved in activation of AAV gene transcription, stage specific AAV mRNA splicing, AAV DNA replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Parvoviruses,* vol. I (P. Tijssen, ed.); Muzyczka, N. (1992) *Current Topics. Microbiol. and Immun.* 158, 97–129. Specifically, early adenoviral E1A, E1B 55K, E2A, E4, and VA RNA gene regions are thought to participate in the accessory process. Janik et al. (1981) *Proc. Natl. Acad. Sci. USA* 78, 1925–1929. Herpesvirus-derived accessory functions have been described. See, e.g., Young et al. (1979) *Prog. Med. Virol.* 25, 113. Vaccinia virus-derived accessory functions have also been described. See, e.g.,Carter, B. J. (1990), supra., Schlehofer et al (1986) *Virology* 152, 110–117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon, cosmid or virus that has been modified from its naturally occurring form.

By "supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not lower than about 200-fold less than the amount obtained using adenovirus infection, more preferably not lower than about 100-fold less, and most preferably equal to, or greater than, the amount obtained using adenovirus infection.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsulating a heterologous nucleotide sequence of interest which is flanked on both sides by AAV ITRs. A rAAV virion is produced in a suitable host cell comprising an AAV vector, AAV helper functions and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52, 456; Sambrook et al. (1989) *Molecular Cloning: A Laboratory Manual,* Cold Spring Harbor Laboratories, New York; Davis et al. (1986) *Basic Methods in Molecular Biology,* Elsevier; Chu et al. (1981) *Gene* 13, 197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement to the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which allow for the formation of stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue" or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides-including any single or multiple amino acid additions, substitutions and/or deletions occurring internally or at the amino or carboxy termini thereof—so long as integration activity remains.

A "functional homologue" or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2A gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

The phrase "intact coding region" is used in its usual sense—i.e., a nucleotide sequence that is capable of coding for a specific gene product. As is well recognized in the art, an intact coding region may be disrupted by several types of mutations, including deletions (which eliminate all or part of the coding region), frameshift mutations (which alter the reading frame of the coding region such that the corresponding gene product is truncated or no longer produced), and point mutations (which alter amino acid residues in the corresponding gene product and thus affect its function).

GENERAL METHODS

It is a primary object of the present invention to provide improved accessory function systems and host cells useful in the production of rAAV virions. More particularly, it is an object of the present invention to provide accessory function systems and host cells that support rAAV production but do not contain oncogenic sequences.

In one embodiment, a nucleic acid molecule that provides one or more accessory functions for supporting rAAV virion production in an animal host cell is provided. The nucleic acid molecule includes an adenovirus E4 region but lacks an intact E4 ORF6 coding region. The E4 ORF6 coding region may be disrupted by several types of mutations, including deletions, frameshift mutations, and point mutations. In certain preferred embodiments, the nucleic acid molecule also lacks an intact E4 ORF1 coding region.

The above-described nucleic acid molecules can be prepared and cloned into a suitable vector such as a plasmid or virus particle to provide an AAV accessory function vector. An accessory function vector of the present invention can further include elements that control the replication and expression of the nucleic acid sequences that code for one or more AAV accessory functions.

In other embodiments, the present invention includes accessory function systems which allow for the efficient production of rAAV virions in the absence of infection with a helper virus. Unlike prior production methods, the accessory functions of the present invention are provided by introducing one or more vectors, such as plasmids, which contain genes required for rAAV virion production, into a host cell. In this manner, the present accessory function systems can support the production of commercially significant levels of rAAV virions without significant levels of contaminating helper virus particles, or other contaminating virus products (e.g., the adenoviral fiber protein). Efficient production of rAAV virions is achieved when rAAV virion yields are obtained at levels that are not lower than about 200-fold less than levels obtained when using adenovirus type-2 infection to provide the accessory functions.

The accessory functions are provided on one or more vectors. The vector(s) will include adenoviral-derived nucleotide sequences necessary for rAAV virion production. As explained further below, the sequences present on the accessory function construct(s) will be determined by the host cell used and can include E1A, E1B, E2A, E4 and VA RNA regions.

The accessory function vectors of the invention can alternatively include one or more polynucleotide homologues which replace the adenoviral gene sequences, so long as each homologue retains the ability to provide the accessory functions of the replaced adenoviral gene. Thus, homologous nucleotide sequences can be derived from another adenoviral serotype (e.g., adenovirus type-2), from another helper virus moiety (e.g. a herpesvirus or vaccinia virus), or can be derived from any other suitable source.

Further, accessory function vectors constructed according to the invention can be in the form of a plasmid, phage, transposon, cosmid, or recombinant virus. Alternatively, the vector can be in the form of one or more linearized DNA or RNA fragments which, when associated with the appropriate control elements and enzymes, can be transcribed or expressed in a host cell to provide accessory functions. All of the above-described vectors can be readily introduced into a suitable host cell using transfection techniques that are known in the art. Such transfection methods have been described, including calcium phosphate co-precipitation (Graham et al. (1973) *Virol.* 52:456–467), direct microinjection into cultured cells (M. R. Capecchi (1980) *Cell* 22:479–488), electroporation (Shigekawa et al. (1988) *BioTechniques* 6:742–751), liposome mediated gene transfer (Mannino et al. (1988) *BioTechniques* 6:682–690), lipid-mediated transfection (Felgner et al. (1987) *Proc. Natl. Acad Sci. USA* 84:7413–7417), and nucleic acid delivery using high-velocity microprojectiles (Klein et al. (1987) *Nature* 327:70–73).

Accessory function vectors can be engineered using conventional recombinant techniques. Particularly, nucleic acid molecules can be readily assembled in any desired order by inserting one or more accessory function nucleotide sequences into a construct, such as by ligating restriction fragments or PCR-generated products into a cloning vector using polylinker oligonucleotides or the like. The newly formed nucleic acid molecule can then be excised from the vector and placed in an appropriate expression construct using restriction enzymes or other techniques that are well known in the art.

More particularly, selected adenoviral genes or gene regions (e.g., E1A, E1B, E2A, E4 and VA RNA), or functional homologues thereof, can be excised either from a viral genome or from a vector containing the same. Alternatively, selected adenoviral genes or gene regions may be generated as PCR products using as a template either viral DNA or a vector containing such DNA. The genes or gene regions are then inserted into a suitable vector either individually or linked together to provide an accessory function construct using standard ligation techniques such as those described in Sambrook et al., supra. Such constructs can be engineered to include three nucleic acid molecules derived from the adenovirus type-5 genome: a VA RNA-containing region, an E2A-containing region, and an E4-containing region.

Nucleic acid molecules comprising one or more accessory functions can also be synthetically derived using a combination of solid phase direct oligonucleotide synthesis chemistry and enzymatic ligation methods that are conventional in the art. Synthetic sequences may be constructed having features such as restriction enzyme sites, and can be prepared in commercially available oligonucleotide synthesis devices such as those devices available from Applied Biosystems, Inc. (Foster City, Calif.) using the phosphoramidite method. See, e.g., Beaucage et al. (1981) Tetrahedron Lett 22:1859–1862. The nucleotide sequence of the adenovirus type-2 genome is generally known, and is publicly available (e.g., as GeneBank Reference Name: ADRCG, Accession Number: J01917; and as NCBI Identification Number: 209811). The nucleotide sequence of the adenovirus type-5 genome is believed to be 99% homologous to the adenovirus type-2 genome. Preferred codons for expression of the synthetic molecule in mammalian cells can also be readily synthesized. Complete nucleic acid molecules are then assembled from overlapping oligonucleotides prepared by the above methods. See, e.g., Edge, Nature 292, 756 (1981); Nambair et al., Science 223, 1299 (1984), Jay et al., J. Biol. Chem. 259, 6311 (1984).

When adenoviral gene regions are used in the vectors of the present invention to provide accessory functions, those regions will be operably linked to control sequences that direct the transcription or expression thereof. Such control sequences can comprise those adenoviral control sequences normally associated with the gene regions in the wild-type adenoviral genome. Alternatively, heterologous control sequences can be employed where desired. Useful heterologous promoter sequences include those derived from sequences encoding mammalian genes or viral genes. Examples include, but are not limited to, homologous adenoviral promoters, the SV40 early promoter, mouse mammary tumor virus LTR (MMTV LTR) promoter, adenovirus major late promoter (Ad MLP), a herpes simplex virus (HSV) promoter, a cytomegalovirus (CMV) promoter (e.g., the CMV immediate early promoter region), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

Furthermore, the vectors of the present invention can be constructed to include selectable markers. Suitable markers include genes which confer antibiotic resistance or sensitivity, or impart color, or change the antigenic characteristics when cells which have been transfected with the nucleic acid constructs are grown in an appropriate selective medium. Particular selectable marker genes useful in the practice of the invention include the Neomycin resistance gene (encoding Aminoglycoside phosphotranferase (APH)) that allows selection in mammalian cells by conferring resistance to G418 (available from Sigma, St. Louis, Mo.) and the Hygromycin-B resistance gene (encoding Hygromycin-B-phosphotransferase (HPH)) that confers resistance to Hygrogmycin-B. Other suitable markers are known to those of skill in the art.

The accessory function vectors of the present invention can be used in a variety of systems for rAAV virion production. For example, suitable host cells that have been transfected with one or more accessory function vectors are rendered capable of producing rAAV virions when co-transfected with an AAV vector and an AAV helper construct capable of being expressed in the cell to provide AAV helper functions. The AAV vector, AAV helper construct and the accessory function vector(s) can be introduced into the host cell, either simultaneously or serially, using transfection techniques described above.

AAV vectors used to produce rAAV virions for delivery of a nucleotide sequence of interest can be constructed to include one or more heterologous nucleotide sequences flanked on both ends (5' and 3') with functional AAV ITRS. In the practice of the invention, an AAV vector generally includes at least one AAV ITR and an appropriate promoter sequence suitably positioned relative to a heterologous nucleotide sequence, and at least one AAV ITR positioned downstream of the heterologous sequence. The 5' and 3' ITRs need not necessarily be identical to, or derived from, the same AAV isolate, so long as they function as intended.

Suitable heterologous nucleotide sequences for use in AAV vectors include any functionally relevant nucleotide sequence. Thus, AAV vectors for use in the practice of the invention can include any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function.

AAV vectors can also include control sequences, such as promoter and polyadenylation sites, as well as selectable markers or reporter genes, enhancer sequences, and other control elements which allow for the induction of transcription. Such AAV vectors can be constructed using techniques well known in the art.

In the methods of the invention, AAV helper constructs are used to complement AAV functions deleted from an AAV vector. A number of suitable AAV helper constructs have been described, including, e.g., the plasmids pAAV/Ad and pIM29+45, which encode both rep and cap expression products. See, e.g., Samulski et al. (1989) J. Virol. 63:3822–3828; McCarty et al. (1991) J. Virol. 65:2936–2945. Complementing AAV helper functions in this manner to support rAAV virion production is an art-accepted technique.

Materials and Methods

Plasmid construction pladeno 5 contains the E2A, E4, and VA RNA regions derived from purified adenovirus-2 CO DNA (Boehringer Mannheim, Indianapolis, Ind.). This plasmid was assembled as follows: pBSII S/K+ was modified to replace a 637 bp region, which encodes the polylinker and alpha complementation cassette, with a single EcoRV site using oligonucleotide-directed mutagenesis with an oligonucleotide having the sequence 5'-CCGCTACAGGGCGCGATATCAGCTCACTCAA-3' (Seq ID No:1). A polylinker with the sequence 5'-GGATCCGGTACCGCCCGGGCTCTAGAATCGATG TATACGTCGACGTTTAAACCATA TG-3' (Seq ID No:2), which contains BamHI, KpnI, SrfI, XbaI, ClaI, Bst1107I, SalI, PmeI, and NdeI restriction sites, was then cloned into the EcoRV site. Adenovirus-2 DNA was digested and restriction fragments encoding the E2A region (a 5,335 bp, KpnI-SrfI fragment corresponding to positions 22,233–27,568 of the adenovirus-2 genome) and the VA RNAs (a 731 bp, EcoRV-SacII fragment corresponding to positions 10,426–11,157 of the adenovirus-2 genome) were isolated. The E2A fragment was installed between the SalI and KpnI sites of the polylinker. An E4 region was first assembled in pBSII S/K+ by ligating a 13,864 bp, BamHI-AvrII fragment corresponding to adenovirus-2 positions 21,606–35,470 (encoding the 5' end of the gene) and a 462 bp, AvrII and SrfI, digested PCR fragment corresponding to adenovirus-2 positions 35,371–35,833 (encoding the 3' end of the gene) between the BamHI and SmaI sites of pBSII S/K+. The oligonucleotides used to produce the PCR fragment were designed to introduce a SrfI site at the junction where the E4 promoter and the adenovirus terminal repeat intersect and have the sequences 5'-AGAGGCCCGGGCGTTTT AGGGCGGAGTAACTTGC-3' (Seq ID No:3) and 5'-ACATACCCGCAGGCGTAGAGAC-3' (Seq ID No:4). The intact E4 region was excised by cleavage with SrfI and SpeI and the 3,189 bp fragment corresponding to adenovirus-2 positions 32,644–35,833 was cloned into the E2A intermediate between the SrfI and XbaI sites. Finally, the VA RNA fragment was inserted into the Bst1107 site after T4 polymerase-mediated blunt end modification of the SacII site. The genes in pladeno 5 are arranged such that the 5' ends of the E2A and E4 promoters abut, causing the regions to transcribe away from each other in opposite directions. The VA RNA genes, which are located at the 3' end of the E4 gene, transcribe towards the E4 gene. The plasmid is 11,619 bp in length.

pE4 was produced by cloning the 3,185 bp SrfI-ClaI fragment from pladeno 5 between the SmaI and ClaI sites of pBSII S/K+, respectively.

pVAE2A was produced by cleaving pladeno 5 with SrfI and ClaI to produce 8,434 bp (VA and E2A encoding) fragments. These fragments were blunt-end modified using Klenow fragment and autoligated.

pCMVE4orf6 expresses E4 ORF 6 using the CMV immediate early (IE) promoter. It was created by cloning the approximately 1024 bp, BglII-SmaI fragment encoding the ad-5 E40RF6 gene (ad-2 positions 34,115–33,091) into the expression plasmid p3.3c. The expression cassette of p3.3c is composed of the CMV IE promoter followed by the first intron from the human growth hormone gene, a cloning site for the gene to be expressed, and the SV40 late polyadenylation site. The construct expresses only the E40RF6 gene and does not express E40RF6/7.

pW4389lacZ comprises (in order around the plasmid) an ITR-bounded CMV-driven lacZ expression cassette, a β-lactamase gene, the AAV-2 rep and cap genes, and a colEl origin of replication. To construct pW4389lacZ, pUC119 was cut with AflIII and partially digested with BspHI, blunt end modified with the Klenow enzyme, and ligated to form a circular 1,732 bp plasmid containing the bacterial origin and the amp gene only (the polylinker and F1 origin were removed). The blunted and ligated AflIII and BspHI cuts form a unique NspI site. The plasmid was then cut with NspI, blunt end modified with T4 polymerase, and the 20 bp, HindIII-HincII fragment (made blunt with the Klenow enzyme) from the pUC119 polylinker was ligated into it. The HindIII site from the blunted polylinker was regenerated and was positioned adjacent to the bacterial origin of replication. The resulting plasmid was cut at the unique Sse8387I site and an Sse8387I-PvuII-Sse8387I oligonucleotide, 5'-GGCAGCTGCCTGCA-3' (Seq ID No:5), was ligated in. The remaining unique BspHI site was cut, blunted with Klenow enzyme, and the AscI oligonucleotide, 5'-GAAGGCGCGCCTTC-3' (Seq ID No:6), was ligated into it, eliminating the BspHI site. This plasmid was called pWee. In order to create pWlacZ, an expression cassette that was flanked by AAV-2 ITRs, and that consisted of the CMV IE promoter, the hGH first intron, the adhlacZ gene (Clontech, Palo Alto, Calif.), and the SV40 early polyadenylation site, was installed in the unique PvuII site of pWee such that the CMV promoter was proximal to the bacterial amp gene of pWee. The construction of this expression cassette has been previously described. pW4389lacZ was created by linkering a DNA fragment that encodes the entire AAV-2 genome excluding the ITR sequences (AAV-2 base pairs 146–4534) with AscI linkers (5'-GAAGGCGCGCCTTC-3' (Seq ID No:7)) and ligating the linkered rep/cap fragment into the unique AscI site of pWlacZ. The AAV-2 gene encoding segments were oriented such that the rep gene is proximal to the bacterial origin of replication.

pladeno 5Δorf 6 is identical to pladeno 5 except the ORF 6-specific sequences are deleted (bases equivalent to bases 33,193–33,903 of adenovirus-2). This plasmid contains all of the E4 ORFs, including ORF 6/7, but makes no ORF 6. pladeno5 was digested with ClaI and AvrII, dephosphorylated, and the 8787 bp E2A and VA RNA encoding fragment was isolated. The following pairs of PCR primers were used to produce E4-encoding DNA fragments using pladeno 5 as template: 67A and 67B (5'-CTGTGGAAGCGCTGTATGTT-3' (Seq ID No:8) and 5'-GTCCACGCGTTGTGCATTGTCAAAGTGT-3' (Seq ID No:9), respectively) and 67C and 67D (5'-CACAACGCGTGGACTTCCCCTTGCCC-3' (Seq ID No:10) and 5'-AGAGCAGCGGCAGACATGCA-3' (Seq ID No:11), respectively). Reactions with primers 67A and 67B produced a product of 1627 bp, while reactions with primers 67C and 67D produced a 628 bp product. The PCR products were digested with AvrII and MluI, and MluI and ClaI, respectively, and 1570 bp and 551 bp fragments were isolated, respectively. These fragments, along with 8787 bp fragment described above, were ligated in a three part ligation, and pladeno 5Δorf 6 was produced.

pladeno 5Δorf 1+6 was constructed from pladeno 5Δorf 6, and contains a large deletion in E4 ORF 1 (equivalent to bases 35,323–35,510 of adenovirus-2) as well as no ORF 6-specific sequences. Aliquots of pladeno 5Δorf 6 were digested with Eco47III and SpeI, and SpeI, HpaI, and alkaline phosphatase. 758 bp (Eco47III-SpeI) and 9,963 bp (SpeI-HpaI) fragments were isolated and ligated to form pladeno 5Δorf 1+6.

pCMVE4orf6/7 is a CMV IE-driven construct expressing only ORF 6/7 from adenovirus-2. Pladeno 5Δorf6 was digested with BglII and NsiI, and the 886 bp fragment encoding ORF 6/7, the E4 polyadenylation site and 115 bp of noncoding sequence that flanks the VA RNAs (adenovirus-2 positions 34,115–33,903 and 33,193–32,644, which together comprise ORF 6/7 and its polyadenylation site and positions 11,044–11,159 which are VA RNA flanking sequences). This fragment was ligated to p3.3.1c digested with BamHI and PstI, to produce pCMVE4orf6/7.

AAV Vector Production and Titration 293 cells (5×10$^6$ cells plated on a 10 cm dishes) were transfected with pW4389lacZ in the presence or absence of various combinations of the adenoviral helper plasmids listed above. The transfections were done by the calcium phosphate method of M. Wigler et al., *Proc. Natl. Acad Sci. USA* 76:1373 (1979), using a total of 30 micrograms of DNA for a period of 6 hours. For each transfection, 10 micrograms of pW4389lacZ was used in combination with 10 micrograms of each of the adenoviral helper plasmids. If the total amount of required plasmid DNA amounted to less than 30 micrograms, pBluescript II S/K+ was added to bring the total amount of transfected DNA to 30 micrograms. After the transfection period, the media were changed, and the cultures were incubated at 37° C. for 18 hours. At this time, the serum-containing media was replaced with serum- free medium and the cultures were incubated for another 54 hours (72 hours total). The cells were then collected, the media removed by centrifugation (1000×g for 10 min.), and a lysate was produced using 3 freeze/thaw cycles (alternating between dry ice-ethanol and 37° C. baths). The lysates were made free of debris by centrifugation (10,000×g for 10 min). All adenoviral helper transfections were done in duplicate. The transfection efficiency was approximately 70%. This transfection efficiency is consistently obtained irrespective of cell passage or flask size provided that the cells are at least 3 passages from frozen storage and they are never allowed to reach confluency. AAV lacZ vector production was assessed by titration of the freeze/thaw extracts or purified vector preparations using 293 cells in the presence of an adenovirus-2 superinfection (MOI=50). The transduced cultures were incubated for 24 hours at 37° C. before fixation and X-gal staining. The stained cells were counted under light microscopy.

6. EXAMPLES

The following example is given to illustrate one embodiment which has been made of the present invention. It is to be understood that the following example is neither comprehensive nor exhaustive of the many types of embodiments which can be prepared in accordance with the present invention.

Example 1

Versions of pladeno 5 lacking E4 ORF 6, E4 ORFs 1 and 6, or the entire E4 region, were tested for the ability to mediate AAV vector production using pW4389lacZ as both a lacZ vector and as a source of rep and cap genes. The pladeno 5 deletion mutants were also tested in the presence of plasmids that express some or all of the corresponding deleted ORFs. These data are summarized in Table 1 below.

TABLE 1

| Adenoviral Helper Plasmid(s) | AAVlacZ vector titer[†] |
|---|---|
| pladeno 5 | 1.3 × 10$^9$ |
| pladeno 5 Δorf 6 | 1.1 × 10$^9$ |
| pladeno 5 Δorf 1 + 6 | 8 × 10$^8$ |
| pladeno 5 ΔE4 | 5.1 × 10$^7$ |
| pladeno 5 Δorf 6 and pE4 | 8.1 × 10$^8$ |
| pladeno 5 Δorf 6 and pCMVE4 orf 6 | 1.2 × 10$^9$ |
| pladeno 5 orf 1 + 6 and pE4 | 7 × 10$^8$ |
| pladeno 5 ΔE4 and pE4 | 4.6 × 10$^8$ |
| pladeno 5 ΔE4 and pCMVE4 orf 6 | 5.1 × 10$^8$ |
| pladeno 5 ΔE4 and pCMVE4 orf 6/7 | 2.8 × 10$^7$ |

[†]As determined by the lacZ assay.

The elimination of the oncogenic genes in AAV helper plasmids may result in safer AAV vector preparations. Deletion of the two potentially oncogenic genes, E4 ORFs 1 and 6, resulted in only minor reductions in AAV vector production. Complementation of the ORF 1- and ORF 6- deleted pladeno 5 mutants with an E4 plasmid did not augment their production activity, indicating that this minor reduction in vector production may be due to intra-assay error. In contrast, deletion of the entire E4 region caused a 25-fold reduction in AAV vector production. These data indicate that the E4 contains at least two separate activities that augment AAV vector production in 72 hour cultures. These activities are provided by (1) E4 ORF 6 and (2) the E4 region lacking ORFs 1 and 6 or some subset of these genes. The data above indicate that expression of E4 ORF 6/7 alone does not produce this activity.

In summary, the present invention relates to accessory function systems and host cells for use in the production of rAAV. The accessory function systems and host cells of the present invention allow the production of rAAV without the use of infectious helper virus and eliminate the risk of transmitting oncogenic nucleotide sequences.

As described above, the present invention also relates to an adenovirus E4 region that lacks the putative oncogenic sequences coded by ORF1 and ORF6. The present invention further includes rAAV produced using the accessory function systems described above.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A nucleic acid molecule which provides one or more accessory functions for supporting recombinant AAV (rAAV) virion production in an animal host cell, said nucleic acid molecule comprising an adenovirus E4 region, wherein said nucleic acid molecule lacks an intact E4 ORF 6 coding region.

2. An accessory function vector comprising the nucleic acid molecule of claim 1.

3. The accessory function vector of claim 2, wherein said vector is a plasmid.

4. The accessory function vector of claim 3, wherein said nucleotide sequence is operably linked to a heterologous promoter.

5. A host cell comprising the nucleic acid molecule of claim 1.

6. The host cell of claim 5 further comprising AAV helper genes.

7. The nucleic acid molecule of claim 1, wherein said nucleic acid molecule also lacks an intact adenovirus E4 ORF 1 coding region.

8. An accessory function vector comprising the nucleic acid molecule of claim 7.

9. The accessory function vector of claim 8, wherein said vector is a plasmid.

10. The accessory function vector of claim 9, wherein said nucleotide sequence is operably linked to a heterologous promoter.

11. A host cell comprising the accessory function vector of claim 8.

12. The host cell of claim 11 further comprising AAV helper genes.

13. A nucleic acid molecule which provides one or more accessory functions for supporting recombinant AAV (rAAV) virion production in a host cell, said nucleic acid molecule comprising: (i) an adenovirus E4 ORE 2 coding region, (ii) an adenovirus E4 ORE 3 coding region, (iii) an adenovirus E4 ORE 3/4 coding region, (iv) an adenovirus E4 ORF 4 coding region, and (v) an adenovirus E4 ORF 6/7 coding region, wherein said nucleic acid molecule lacks an intact adenovirus E4 ORF6 coding region.

14. An accessory function vector comprising the nucleic acid molecule of claim 13.

15. The accessory function vector of claim 14, wherein said vector is a plasmid.

16. The accessory function vector of claim 15, wherein said nucleotide sequence is operably linked to a heterologous promoter.

17. A host cell comprising the accessory function vector of claim 14.

18. The host cell of claim 17 further comprising AAV helper genes.

19. The nucleic acid molecule of claim 13, wherein said nucleic acid molecule also lacks an intact adenovirus E4 ORF 1 coding region.

20. An accessory function system for recombinant AAV (rAAV) virion production, said accessory function system comprising first, second, and third accessory function vectors, wherein:

(a) said first accessory function vector comprises a nucleotide sequence that provides adenovirus VA RNAs;

(b) said second accessory function vector comprises an adenovirus E4 region, wherein said adenovirus E4 region lacks an intact E4 ORF 6 coding region;

(c) said third accessory function vector comprises an adenovirus region coding for the E2A 72 kD protein.

21. A method of producing recombinant AAV (rAAV) virions comprising:

(a) introducing an AAV vector into a suitable host cell;

(b) introducing an AAV helper construct into the host cell, said helper construct comprising AAV coding regions that are expressed in the host cell to complement AAV helper functions missing from said AAV vector;

(c) introducing the accessory function system of claim 20 into the host cell, said accessory function system providing accessory functions for supporting rAAV virion production in the host cell; and (d) culturing the host cell to produce rAAV virions.

* * * * *

UNITED STATES PATENT AND TRADEMARK OFFICE
CERTIFICATE OF CORRECTION

PATENT NO.   : 5,945,335
DATED        : August 31, 1999
INVENTOR(S)  : Colosi

It is certified that error appears in the above-identified patent and that said Letters Patent is hereby corrected as shown below:

In column 23, line 1, please change "E4 ORE" to --E4 ORF--.

In column 23, line 2, please change "E4 ORE" to --E4 ORF--.

In column 23, line 3, please change "E4 ORE" to --E4 ORF--.

Signed and Sealed this

Thirteenth Day of June, 2000

Attest:

Attesting Officer

Q. TODD DICKINSON

Director of Patents and Trademarks

SEQUENCE LISTING

<160> NUMBER OF SEQ ID NOS: 11

<210> SEQ ID NO 1
<211> LENGTH: 31
<212> TYPE: DNA

-continued

<213> ORGANISM: Artificial Sequence
<220> FEATURE:
<223> OTHER INFORMATION: Description of Artificial Sequence:
      oligonucleotide

<400> SEQUENCE: 1
ccgctacagg gcgcgatatc agctcactca a                                    31

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
ggatccggta ccgcccgggc tctagaatcg atgtatacgt cgacgtttaa accatatg       58

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
agaggcccgg gcgttttagg gcggagtaac ttgc                                 34

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
acatacccgc aggcgtagag ac                                              22

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ggcagctgcc tgca                                                       14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gaaggcgcgc cttc                                                       14

<210> SEQ ID NO 7
<211> LENGTH: 14
<212> TYPE: DNA
<213> ORGANISM: Artificial Sequence
<220> FEATURE:

-continued

```
<223> OTHER INFORMATION: Description of Artificial Sequence:
        oligonucleotide

<400> SEQUENCE: 7
gaaggcgcgc cttc                                                    14

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
        oligonucleotide

<400> SEQUENCE: 8
ctgtggaagc gctgtatgtt                                              20

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
        oligonucleotide

<400> SEQUENCE: 9
gtccacgcgt tgtgcattgt caaagtgt                                     28

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:
        oligonucleotide

<400> SEQUENCE: 10
cacaacgcgt ggacttcccc ttgccc                                       26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
        oligonucleotide

<400> SEQUENCE: 11
agagcagcgg cagacatgca                                              20
```